United States Patent [19]

Takahashi et al.

[11] 4,332,718

[45] Jun. 1, 1982

[54] PROCESS FOR PRODUCING AN α-L-ASPARTYL-L-PHENYLALANINE LOWER ALKYL ESTER

[75] Inventors: Satoji Takahashi, Kawasaki; Koji Toi, Hayamamachi, both of Japan

[73] Assignee: Ajinomoto Company, Inc., Tokyo, Japan

[21] Appl. No.: 126,671

[22] Filed: Mar. 4, 1980

Related U.S. Application Data

[63] Continuation-in-part of Ser. No. 66,656, Aug. 15, 1979, abandoned.

[30] Foreign Application Priority Data

Sep. 5, 1978 [JP] Japan ................................ 53-108962

[51] Int. Cl.$^3$ .................. C07C 103/52; C07D 307/60
[52] U.S. Cl. ............................... 260/112.5 R; 549/253
[58] Field of Search ................... 260/112.5 R, 346.74; 549/253

[56] References Cited

U.S. PATENT DOCUMENTS

| B 485,972 | 3/1976 | Farkas et al. | 260/112.5 R |
|---|---|---|---|
| 3,462,460 | 8/1969 | Kollonitsch | 260/346.74 |
| 3,808,190 | 4/1974 | Dahlmans et al. | 260/112.5 R |
| 3,872,110 | 3/1975 | Ariyoshi et al. | 260/346.74 |
| 3,901,871 | 8/1975 | Anderson | 260/112.5 R |
| 3,933,781 | 1/1976 | Bachman et al. | 260/112.5 R |
| 3,948,971 | 4/1976 | Veber et al. | 260/112.5 R |
| 3,962,207 | 6/1976 | Uchiyama et al. | 260/112.5 R |
| 4,017,472 | 4/1977 | Farkas et al. | 260/112.5 R |

FOREIGN PATENT DOCUMENTS

| 1143516 | 2/1963 | Fed. Rep. of Germany ... 260/112.5 R |
|---|---|---|
| 2107358 | 2/1971 | Fed. Rep. of Germany ...... 549/253 |
| 1243169 | 8/1971 | United Kingdom ......... 260/112.5 R |

OTHER PUBLICATIONS

Derwitt abstr. of Japanese Pat. No. J5-5035-059, Sep. 5, 1978.
Chem. Abstr., vol. 78, (1973), 111764g, 98023e.
Chem. Abstr., vol. 80, (1974), 27474w.
Chem. Abstr., vol. 79, (1973), 66803b.
Chem. Abstr., vol. 84, (1976), 31506h.
Chem. Abstr., vol. 85, (1976), 6056x.

*Primary Examiner*—Delbert R. Phillips
*Attorney, Agent, or Firm*—Oblon, Fisher, Spivak, McClelland & Maier

[57] ABSTRACT

A process for producing an α-L-aspartyl-L-phenylalanine lower alkyl ester or its hydrochloride which comprises (a) treating an L-N-(1-methyl-2-lower aliphatic acylvinyl or 1-methyl-2-lower alkoxycarbonylvinyl)-aspartic acid or an alkali metal salt thereof with a dehydrating agent in an organic solvent containing an acid, (b) reacting the solution resulting from such treatment with an L-phenylalanine lower alkyl ester and (c) treating the resulting reaction mixture with water or an aqueous acid solution to remove the 1-methyl-2-lower aliphatic acylvinyl or 1-methyl-2-lower alkoxycarbonylvinyl group from the L-N-(1-methyl-2-lower aliphatic acylvinyl or 1-methyl-2-lower alkoxycarbonylvinyl)-aspartyl-L-phenylalanine lower alkyl ester is disclosed, along with L-N-(1-methyl-2-acetylvinyl)-aspartic acid anhydride.

3 Claims, No Drawings

PROCESS FOR PRODUCING AN α-L-ASPARTYL-L-PHENYLALANINE LOWER ALKYL ESTER

This application is a continuation-in-part of Ser. No. 066,656, filed Aug. 15, 1979, now abandoned.

FIELD OF THE INVENTION

This invention relates to a process for producing an α-L-aspartyl-L-phenylalanine lower alkyl ester.

An α-L-aspartyl-L-phenylalanine lower alkyl ester is a new excellent sweetener possessing a strongly sweet sugar-like taste.

DESCRIPTION OF THE PRIOR ART

Heretofore, there have been proposed several methods for synthesis of the compound. According to one method, the α-carboxyl group of L-aspartic acid whose amino and β-carboxyl groups are both protected is first converted to a very reactive ester, the ester is then condensed with L-phenylalanine methyl ester, and the protecting groups are finally removed. See Dutch published unexamined patent application No. 6800870. This method is, however, industrially disadvantageous, because it involves many reaction steps and needs many kinds of auxiliary raw materials. There is another method in which L-aspartic acid, whose amino group is protected by a benzyloxycarbonyl group, is first dehydrated to L-N-benzyloxycarbonyl-aspartic acid anhydride, the anhydride is then condensed with L-phenylalanine methyl ester, and the protecting group is finally removed. This second method also has some defects from the industrial point of view. For example, the protecting agent is expensive and a dangerous reductive reaction is applied to remove the protecting group. There is a third method in which L-aspartic acid is first converted to its anhydride hydrochloride, and the hydrochloride is then condensed with L-phenylalanine methyl ester. This third method is, however, industrially defective in that the removal of the by-products from condensation reaction is very troublesome.

This invention relates to an industrially advantageous new synthetic process which obviates such above-mentioned defects involved in the heretofore known methods.

Indeed, it is generally disclosed in German Pat. No. 1143516 that an amino acid and acetylacetone are reacted with one another in the presence of an alkali to obtain the N-(1-methyl-2-acetylvinyl) amino acid or its alkali salt, but no specific mention is made in the patent or any other publications of the preparation of an L-N-(1-methyl-2-lower aliphatic acylvinyl or 1-methyl-2-lower alkoxycarbonylvinyl)-aspartic acid from L-aspartic acid.

SUMMARY OF THE INVENTION

The present inventors have, on the basis of the disclosure, found that such N-substituted L-aspartic acids or their alkali metal salts can be obtained from L-aspartic acid. They have further found that an α-L-aspartyl-L-phenylalanine lower alkyl ester can be easily synthesized in high yields in the following way: an N-substituted L-aspartic acid or its alkali metal salt is treated in an organic solvent with a dehydrating agent to give the corresponding acid anhydride, the anhydride is then reacted with an L-phenylalanine lower alkyl ester to give the corresponding N-substituted dipeptide lower alkyl ester, and the last-mentioned reaction product is treated with an acid to remove the N-protecting group. The present invention has been made on the basis of these findings.

DESCRIPTION OF THE PREFERRED EMBODIMENTS

It is to be noted that, though the process of this invention involves a few reaction steps, a product obtained in a reaction step may, without being isolated from the remainder of the reaction mixture resulting from the reaction step, be subjected, if accompanied by no particular disadvantages, to the following reaction step, as will be apparent from the description made hereinafter.

Examples of L-N-(1-methyl-2-lower alphatic acylvinyl or 1-methyl-2-lower alkoxycarbonylvinyl)-aspartic acids are L-N-(1-methyl-2-acetylvinyl or propionylvinyl)-aspartic acid, and L-N-(1-methyl-2-methoxycarbonylvinyl, ethoxycarbonylvinyl, propoxycarbonylvinyl or butoxycarbonylvinyl)-aspartic acid. These compounds may be used as such or as their salts such as alkali metal salts.

These N-substituted (i.e., N-protected) L-aspartic acids or their salts may be synthesized in the following way: L-aspartic acid is dissolved in a lower alcohol such as methanol or ethanol, together with at least an equimolecular amount of a diketone such as acetylacetone, or methyl or ethyl acetoacetate and an alkali such as caustic soda or potash in an amount of 0.1–5, preferably 0.5–2.5, equivalents to L-aspartic acid, the resulting solution is concentrated or mixed with a solubility-lowering solvent such as acetone, whereby the N-substituted L-aspartic acid is crystallized as its alkali metal salt, and the alkali metal salt crystals are finally separated. An amine such as triethylamine or triethanolamine may be used instead of a caustic alkali.

Examples of dehydrating agents are lower fatty acid anhydride such as acetic anhydride, a lower fatty acid halide such as acetyl chloride, a phosphorus halogenide such as phosphorus trichloride, phosphorus oxygen acid halide such as phosphorus oxychloride, a sulfur oxygen acid halide such as thionyl chloride or sulfonyl chloride, and a haloformic acid ester such as ethyl chloroformate.

A dehydrating agent suffices when used in an amount sufficient to convert L-N-(1-methyl-2-lower aliphatic acylvinyl or 1-methyl-2-lower alkoxycarbonylvinyl)-aspartic acid to the inner anhydride. For example, a lower fatty acid anhydride, a lower fatty acid halide, a sulfur oxygen acid halide or a haloformic acid ester is used in 0.5–3.0, preferably 0.8–2.0, times an amount equimolecular with the N-substituted L-aspartic acid, and a phosphorus halogenide is used in 0.5–3.0, preferably 0.8–2.0, times an amount of the mole divided by the number of the halogen atoms contained in the phosphorus halogenide molecule per mole of the N-substituted L-aspartic acid. By use of large excess dehydrating agent, the desired compound can be synthesized, but by-products are also produced in large amounts. Use of a large excess dehydrating agent is accordingly undesirable.

Any organic solvents inert to the dehydrating agent may be used in the dehydrating treatment. Examples of such solvents are esters such as ethyl or butyl acetate, hydrocarbons such as benzene, toluene, or xylene, chlorohydrocarbons such as ethylene dichloride. The dehydrating treatment may usually be carried out at temperatures between about −30° C. and about 20° C., preferably between −25° C. and 5° C. depending on the solvent or dehydrating agent employed and other conditions. Racemization of N-substituted aspartic acid anhydride is apt to occur above 5° C. The reaction is slower below −30° C., while side reactions are apt to occur above 20° C. Shorter times suffice at higher temperatures for dehydrating treatment, while longer times are needed at lower temperatures. 5 to 25 hours suffice when the treatment is carried out at between −25° C. and 5° C.

A lower carboxylic acid such as formic acid or acetic acid, or a mineral acid such as hydrogen chloride or sulfuric acid, when mixed with the organic solvent, brings about some favourable effects such as improved efficiency of the dehydrating treatment and prevention of coloration. Further, as will be described hereinafter, when a solution resulting from dehydrating treatment is first reacted with an L-phenylalanine lower alkyl ester and then contacted with an acid, the aimed-at compound, i.e., the α-L-aspartyl-L-phenylalanine lower alkyl ester is produced in a very high yield. A lower carboxylic acid or mineral acid may be used in an amount of less then 10 moles, preferably between 1 and 5 moles per mole of L-N-(1-methyl-2 lower aliphatic acylvinyl or 1-methyl 2-lower alkoxycarbonylvinyl)-aspartic acid. Carrying out the dehydrating reaction outside the abovementioned broader range is undesirable because of lower reaction velocity and lower reaction yield.

The acid anhydride resulting from dehydrating treatment may of course be reacted with an L-phenylalanine lower alkyl ester after being separated from the dehydrating treatment mixture. The reaction is carried out in the presence of an acid, organic or inorganic, whereby an α-L-aspartyl-L-phenylalanine lower alkyl ester is increased in yields. It may also be reacted as it is contained in the mixture. In the latter case, reaction of the solution resulting from the dehydrating treatment with an L-phenylalanine lower alkyl ester may be carried out by adding, to the solution resulting from the dehydrating treatment, an L-phenylalanine lower alkyl ester dissolved in such an organic solvent employable for dehydrating treatment. Reaction temperature is below 50° C. A higher temperature above 50° C. causes side reactions. Room temperature (about 20° C.) may be appropriate. Reaction time of as short as 0.5 to 2 hours suffices, because the reaction proceeds very rapidly. An L-phenylalanine lower alkyl ester is appropriately used in an amount of 0.5 to 2 moles per mole of an N-(1-methyl-2-lower aliphatic acylvinyl or 1-methyl-2-lower alkoxycarbonylvinyl)-L-aspartic acid.

When the solution resulting from reaction with an L-phenylalanine lower alkyl ester is contacted with water or preferably with an aqueous solution containing an acid, the N-protecting group is removed from the N-substituted dipeptide lower alkyl ester contained in the former solution and the formed α- and β-L-aspartyl-L-phenylalanine lower alkyl esters separate out from the organic solvent layer and move into the aqueous layer. To prepare an acid-containing solution, a mineral acid such as hydrochloric acid or sulfuric acid, or a lower carboxylic acid such as acetic acid may be used. Among these acids, hydrochloric acid is the most convenient and the most preferred concentration range is between 0.1 to 2.0 normal. Too high a concentration of an aqueous acid solution brings about undesired crystallization and/or decomposition of the aimed-at compound.

The α-L-aspartyl-L-phenylalanine lower alkyl ester possesses a strongly sweet taste; on the other hand, a β-L-aspartyl-L-phenylalanine lower alkyl ester possesses a weakly bitter taste. Accordingly, it is desired that the former is formed in larger amounts, while the latter in smaller amounts, and that the latter be removed from the former as completely as possible.

According to this invention, an α-L-aspartlyl-L-phenylalanine lower alkyl ester is produced more predominantly than the corresponding β-L-aspartlyl-L-phenylalanine lower alkyl ester, and the invention is very valuable from the industrial point of view.

Separation of an α-L-aspartyl-L-phenylalanine lower alkyl ester from the β-isomer may be carried out in accordance with a known method such as recrystallization. In case of L-aspartyl-L-phenylalanine methyl ester, the α-isomer may be separated as its hydrochloride dihydrate crystals from the last-mentioned aqueous layer, e.g., by adding concentrated hydrochloric acid to the aqueous layer. If a mixture of the α- and β- isomers is first separated from the aqueous layer, e.g., by concentrating, the mixture is dissolved in an appropriate concentration in hydrochloric acid, α-L-aspartlyl-L-phenylalanine methyl ester hydrochloride dihydrate crystallizes out predominantly, and the purpose is efficiently achieved by separating the crystals. α- and β-D-aspartyl-L-phenylalanine methyl esters which may be by-produced in small amounts are removed from the α-isomer, together with the β-isomer by these methods. The hydrochloride dihydrate may in some cases be used as such as a sweetner. If necessary, however, the hydrochloride dihydrate crystals are dissolved in an appropriate concentration in water, and the resulting solution is adjusted in pH with an alkali to crystallize α-L-aspartlyl-L-phenylalanine methyl ester. Highly pure α-L-aspartlyl-L-phenylalanine methyl ester may be obtained in high yields by separating the crystals. See U.S. Pat. No. 3,798,207.

As has been explained hereinabove, the process of this invention involves fewer steps and is easy to operate. In addition to these useful characteristics, an α-L-aspartlyl-L-phenylalanine lower alkyl ester, the aimed-at compound, may be obtained in high yields from L-aspartic acid, one of the main raw materials, according to the process of this invention. The process of this invention is, accordingly, an industrially excellent new process for producing an α-L-aspartlyl-L-phenylalanine lower alkyl ester, whereby a reduction may be made in manufacturing equipment and manufacturing cost, as compared with known methods.

L-N-(1-methyl-2-acetylvinyl)-aspartic acid dialkali metal salt, one of the raw materials of this invention, may be prepared, for example, as under Preparation of Raw Material 1-4 below.

Having now generally described this invention, the same will become better understood by reference to specific examples which are included herein for purposes of illustration only and are not intended to be limiting thereof.

PREPARATION OF RAW MATERIAL 1

To 133 g L-aspartic acid when added 4.0 l methanol, 118 g potassium hydroxide and 110 g acetylacetone and the mixture was stirred overnight at room temperature to give a transparent solution. The solution, after being concentrated under reduced pressure to between one half and one-third of its original volume, was gradually added with 2.0 l acetone with stirring at room temperature and was allowed to stand for 5 hours. The resulting crystals were separated by filtering and dried under reduced pressure in a desiccator to give 235 g L-N-(1-methyl-2-acetylvinyl)-aspartic acid dipotassium salt.

Elemental analysis; Calcd. for $C_9H_{10}N_1O_5K_2$: C, 37.10, H, 3.81; N, 4.81. Found: C, 37.01, H, 3.79; N, 4.85.

A 8.775 g portion of the crystals was dissolved in 80 ml 1 N (one normal) hydrochloric acid, and the solution was concentrated under reduced pressure. The residue was dissolved in 2 N hydrochloric acid to obtain a solution in a total amount of 50 ml. The optical rotation of the solution was measured and calculation of the specific optical rotation of the L-aspartic acid gave $[\alpha]_D^{20} = +26.3°$. This value agrees with that of pure L-aspartic acid.

PREPARATION OF RAW MATERIAL 2

To 101 g L-aspartic acid were added 1.5 l acetylacetone and 232 ml triethylamine and the mixture was stirred overnight at room temperature to give a transparent solution.

The solution was added with a solution of 85.1 g potassium hydroxide in 300 ml methanol with stirring at room temperature. 1 hour after, the resulting crystals were separated by filtration and dried in a desiccator under reduced pressure, whereby 241 g L-N-(1-methyl-2-acetylvinyl)-aspartic dipotassium salt was obtained.

PREPARATION OF RAW MATERIAL 3

133 g L-aspartic acid, 84 g sodium hydroxide and 150 g acetylacetone were suspended in 1.3 l methanol. The mixture was heated under reflux with stirring for 2 hours.

The reaction mixture was then concentrated to about one half of its original volume and allowed to stand overnight at room temperature. The resulting crystals were separated by filtering and dried to give 194 g L-N-(1-methyl-2-acetylvinyl)-aspartic acid disodium salt.

PREPARATION OF RAW MATERIAL 4

To 133 g L-aspartic acid were added 260 g ethyl acetoacetate, 250 ml triethylamine and 1.0 l methanol and the mixture was stirred overnight at room temperature to give a transparent solution. The solution was cooled to 0° C. and 84 g sodium hydroxide was dissolved in it.

The reaction mixture was added with 2.0 l acetone. The formed crystals were separated by filtering and dried under reduced pressure in a desiccator to give 274 g L-N-(1-methyl-2-ethoxycarbonylvinyl)-aspartic acid disodium salt.

Elemental analysis; Calcd. for $C_{10}H_{13}NO_6Na_2$: C, 41.53; H, 4.53; N, 4.84. Found: C, 41.21; H, 4.48; N, 4.90.

A 8.71 g portion of the crystals was dissolved in 80 ml 1 N (one normal) hydrochloric acid, and the solution was concentrated under reduced pressure. The residue was dissolved in 2 N hydrochloric acid to obtain a solution in a total amount of 50 ml. The optical rotation of the solution was measured and calculation of the specific rotation of the L-aspartic acid gave $[\alpha]_D^{20} = +26.4°$. This value agrees with that of pure L-aspartic acid.

EXAMPLE 1

To 292 g L-N-(1-methyl-2-acetylvinyl)-aspartic acid dipotassium salt were added 2.0 l ethyl acetate and 160 ml acetic acid. The mixture was cooled to −6° C. and then stirred at that temperature for 30 minutes. The cooled mixture, after added with 43.7 ml phosphorus trichloride, was stirred for 10 hours.

To the reaction mixture was added a solution heated to 40° C. of 200 g L-phenylalanine methyl ester in 4 l ethyl acetate. The newly resulting mixture was stirred for 30 minutes, then, after added with 1.0 l 1 N (one normal) hydrochloric acid, stirred for additional 1 hour and was allowed to stand, whereby an aqueous layer formed. The aqueous layer was separated. A small portion of it was put aside for analytical use. The remaining aqueous layer was washed by shaking with about 500 ml toluene.

The washed layer was, after cooled to 5° C., added with 150 ml concentrated hydrochloric acid and allowed to stand overnight. The formed needle-like crystals (α-L-aspartyl-L-phenylalanine methyl ester hydrochloride dihydrate) were separated by filtration.

The crystals were added with about 1 l water. The solution was gradually added with aqueous 10% sodium carbonate solution to adjust the pH to 3.0 and heated to 60° C. The heated solution was adjusted in pH to 4.6 with aqueous 10% sodium carbonate solution, cooled to 5° C., and allowed to stand for 5 hours. The formed needle-like crystals (α-L-aspartyl-L-phenylalanine methyl ester hemihydrate) were separated by filtration and dried in a desiccator under reduced pressure. The dried crystals weighed 120 g and tasted strongly sweet.

Two small portions of the crystals were subjected to analysis with an automatic amino acid analyser (Column and fillings; 9φ×100 mm and Hitachi 2611 resin (a cation exchange resin) for one portion to determine α-L-aspartyl-L-phenylalanine methyl ester, and 9φ×550 mm and Hitachi 2613 resin (a cation exchange resin) for the other to determine other substances: Eluting agent; pH 5 citric acid buffer solution: Temperature; 55° C.). α-L-aspartyl-L-phenylalanine methyl ester was only detected and no other substances at all.

Measurement of the specific optical rotation of the crystals gave $[\alpha]_D^{20} = +33.7°$ C. (C=1, acetic acid).

Said small portion of the aqueous layer was subjected to determination of L-aspartyl-L-phenylalanine methyl ester with the same automatic amino acid analyser to reveal the α- and β-isomers in yields of 55% and 40%, respectively, on the basis of the starting N-(1-methyl-2-acetyl-vinyl)-L-aspartic acid dipotassium salt.

EXAMPLE 2

To 260 g L-N-(1-methyl-2-acetyl vinyl)-aspartic acid disodium salt were added 500 ml ethyl acetate and 225 ml acetic acid. The mixture was cooled to −20° C. and added with 125 ml acetic acid anhydride. Reaction was carried on overnight.

The reaction mixture was further treated as in Example 1. 134 g α-L-aspartyl-L-phenylalanine methyl ester was obtained, whose specific optical rotation $[\alpha]_D^{20}$ was +33.6° (C=1, acetic acid).

Determination of L-aspartyl-L-phenylalanine methyl ester revealed the α- and β-isomers in yields of 61% and 37%, respectively, on the basis of the starting N-(1-methyl-2-acetylvinyl)-L-aspartic acid disodium salt.

EXAMPLE 3

5.18 g L-N-(1-methyl-2-acetylvinyl)-aspartic acid disodium salt was added to 50 ml ethyl acetate and the mixture was stirred and cooled to −6° C. The cooled mixture was first added with 0.87 ml phosphorus trichloride and then 1.5 ml formic acid slowly. Reaction was continued for 10 hours.

To the resulting reaction mixture was added 80 ml ethyl acetate solution heated to 35° C. and containing 4 g L-phenylalanine methyl ester. Reaction was continued for 1 hour.

The newly resulting mixture was added with 200 ml 0.5 N hydrochloric acid, stirred for additional 15 minutes and was allowed to stand, whereby an aqueous layer formed. The aqueous layer was separated. The remaining organic layer was, after added with additional 200 ml 0.5 N hydrochloric acid, stirred for 15 minutes and was allowed to stand, whereby another aqueous layer formed. The aqueous layer was separated. Both the aqueous layers were combined and subjected to analysis with the same automatic amino acid analyser as used in Example 1 to determine the L-aspartyl-L-phenylalanine methyl ester. Analysis showed the α-isomer in a yield of 54% and the β-isomer in a yield of 40% on the basis of the starting L-N-(1-methyl-2-acetylvinyl)-aspartic acid disodium salt.

COMPARATIVE EXPERIMENT

Example 3 was repeated except that no acid was added instead of 1.5 ml formic acid. Determination of the L-aspartyl-L-phenylalanine methyl ester revealed the α- and β-isomers in yields of 18% and 10%, respectively.

EXAMPLE 4

Example 3 was repeated except that 1.83 g hydrogen chloride was absorbed instead of 1.5 ml formic acid. Determination of the L-aspartyl-L-phenylalanine methyl ester revealed the α- and β-isomers in yields of 43% and 42%, respectively.

EXAMPLE 5

Example 3 was repeated except that 1.59 ml thionyl chloride was used instead of the phosphorus trichloride and the dehydrating reaction was carried out at −15° C. Determination of L-aspartyl-L-phenylalanine methyl ester showed the α-isomer in a yield of 46% and the β-isomer in a yield of 38%.

EXAMPLE 6

5.83 g L-N-(1-methyl-2-acetylvinyl)-aspartic acid dipotassium salt was dissolved in 50 ml acetic acid. Hydrogen chloride was bubbled through the solution, whereby KCl was precipitated. The KCl precipitate was removed by filtration to give a solution of L-N-(1-methyl-2-acetylvinyl)-aspartic acid in acetic acid. The solution was, after concentrated under reduced pressure to between one-fifth and one-sixth of its original volume, added with 10 ml toluene, cooled to −20° C., and added also with 2.5 ml acetic acid anhydride. Reaction was continued for 24 hours with stirring. To the resulting reaction mixture was added 80 ml toluene solution containing 5 g/dl L-phenylalanine methyl ester at room temperature.

The newly resulting reaction mixture was subjected to the hydrochloric acid treatments as in Example 3. Determination of the L-aspartyl-L-phenylalanine methyl ester showed the α- and β-isomers in yields of 48% and 29%, respectively.

EXAMPLE 7

To 5.78 g L-N-(1-methyl-2-ethoxycarbonylvinyl)-aspartic acid disodium salt were added 50 ml ethyl acetate and 3.2 ml acetic acid. The mixture was stirred and then cooled to −8° C. The cooled mixture, after added with 0.87 ml phosphorus trichloride, was stirred for 10 hours.

To the resulting reaction mixture was added 80 ml ethyl acetate solution heated to 35° C. and containing 4 g L-phenylalanine methyl ester. The reaction was continued for 1 hour.

The newly resulting reaction mixture was then subjected to such hydrochloric acid treatment as in Example 3. Determination of the L-aspartyl-L-phenylalanine methyl ester carried out in the same way as in Example 3 showed the α- and β-isomers in yields of 54% and 39%, respectively.

EXAMPLE 8

A 51.8 g portion of L-N-(1-methyl-2-acetylvinyl)-aspartic acid disodium salt obtained under Preparation of Raw Material 3 was added to a mixture of 500 ml ethyl acetate and 22.6 ml acetic acid. The new mixture was added with 9 ml phosphorus trichloride at −6° C. with stirring. Reaction was continued for 10 hours at the same temperature. An about 45 ml portion of the reaction mixture was added to 25 ml methanol cooled to −10° C. and stirred at −10° C. for 5 hours, whereby all the aspartic acid moiety was methyl-esterified. The esterification reaction mixture was evaporated to dryness under reduced pressure. The residue was added with 60 ml aqueous 2 N sodium hydroxide solution and allowed to stand for 2 hours at room temperature. The mixture was then added with 60 ml 2 N hydrochloric acid and evaporated to dryness. The residue was made to a total volume of 100 ml by adding 2 N hydrochloric acid. The concentration of aspartic acid in the solution was found to be 1.96 g/dl, when measured with an automatic amino acid analyser. The specific optical rotation of the solution $[\alpha]_D^{20}$ was found to be +24.8°. This value means that all the aspartic acid was in the L-form.

The remaining reaction mixture was added with about 1 l acetone cooled to −10° C. and, after being allowed to stand for 1 hour, subjected to filtration. The filtrate was concentrated under a reduced pressure of 10 mmHg to remove 900 ml of the solvent. The residue was added with 250 ml ethyl ether cooled to −10° C. and the resulting oily substance was separated by decantation. The separated oily substance was dissolved in about 300 ml acetone cooled to −10° C. After the insoluble materials were removed, the solution was concentrated under a reduced pressure of 10 mmHg to remove 250 ml of the solvent. Oily substance resulted again upon addition of 200 ml ethyl ether cooled to −10° C. in limited amounts to the residue and was separated by decantation. The solvent was completely removed from the separated oily substance by distillation under reduced pressure, the temperature being kept below −5° C. 12.1 g pure oily substance was obtained.

Elemental analysis; Calcd. for $C_9H_{11}NO_4$: C, 54.82; H, 5.62; N, 7.10. Found: C, 54.31; H, 5.51; N, 7.03.

The oily substance was identified as N-(1-methyl-2-acetylvinyl)-aspartic acid anhydride also by infrared absorption spectrum, nuclear magnetic resonance spectrum, and ultraviolet absorption spectrum.

EXAMPLE 9

To 6.98 g L-N-(1-methyl-2-n-butoxycarbonylvinyl)-aspartic acid dipotassium salt were added 50 ml ethyl acetate and 2.6 ml acetic acid. The mixture was cooled to −6° C. and then stirred at that temperature for 30 minutes. The cooled mixture, after added with 0.88 ml phosphorus trichloride, was stirred for 10 hours.

The reaction mixture was further treated as in Example 3. Determination of the L-aspartyl-L-phenylalanine methyl ester revealed the α-and β-isomers in yields 56% and 39%, respectively.

In this connection, the starting material L-N-(1-methyl-2-n-butoxycarbonylvinyl)-aspartic acid dipotassium salt was prepared as follows;

To 13.3 g L-aspartic acid were added 100 ml methanol, 30.6 ml triethylamine and 19 ml n-butyl acetoacetate and the mixture was stirred overnight at room temperature to give a transparent solution. The solution was cooled to 0° C. and 12.4 g potassium hydroxide was dissolved in it. The reaction mixture, after added with 1.5 l acetone, was stirred at 10° C. for 2 hours. The formed crystals were separated by filtering and dried under reduced pressure in a desiccator to give 26.6 g L-N-(1-methyl-2-n-butoxycarbonylvinyl)-aspartic acid dipotassium salt.

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. A process for producing an α-L-aspartyl-L-phenylalanine lower alkyl ester or its hydrochloride which comprises (a) treating an L-N-(1-methyl-2-lower aliphatic acylvinyl or 1-methyl-2-lower alkoxycarbonylvinyl)-aspartic acid or an alkali metal salt thereof with a dehydrating agent in an organic solvent containing an acid, (b) reacting the solution resulting from such treatment with an L-phenylalanine lower alkyl ester and (c) treating the resulting reaction mixture with water or an aqueous acid solution to remove the 1-methyl-2-lower aliphatic acylvinyl or 1-methyl-2-lower alkoxycarbonylvinyl group from the L-N-(1-methyl-2-lower aliphatic acylvinyl or 1-methyl-2-lower alkoxycarbonylvinyl)-aspartyl-L-phenylalanine lower alkyl ester.

2. A process for producing an α-L-aspartyl-L-phenylalanine lower alkyl ester or its hydrochloride which comprises (a) converting an L-N-(1-methyl-2-lower aliphatic acylvinyl or 1-methyl-2-lower alkoxycarbonylvinyl)-aspartic acid or an alkali metal salt thereof to the corresponding inner anhydride with the use of a dehydrating agent in an organic solvent containing an acid, (b) reacting the anhydride with an L-phenylalanine lower alkyl ester in the presence of an acid, and (c) removing the N-protecting group from the N-substituted dipeptide lower alkyl ester resulting from step (b) with the use of an acid.

3. L-N-(1-methyl-2-acetylvinyl)-aspartic acid anhydride.

* * * * *